United States Patent
Wang et al.

(10) Patent No.: US 10,185,865 B2
(45) Date of Patent: Jan. 22, 2019

(54) FINGERPRINT RECOGNITION DEVICE, MANUFACTURING METHOD THEREOF, LIQUID CRYSTAL DISPLAY

(71) Applicants: BOE TECHNOLOGY GROUP CO., LTD., Beijing (CN); BEIJING BOE DISPLAY TECHNOLOGY CO., LTD., Beijing (CN)

(72) Inventors: Mingchao Wang, Beijing (CN); Junwei Wang, Beijing (CN); Haifeng Yu, Beijing (CN)

(73) Assignees: BOE TECHNOLOGY GROUP CO., LTD., Beijing (CN); BEIJING BOE DISPLAY TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 15/544,863

(22) PCT Filed: Jan. 10, 2017

(86) PCT No.: PCT/CN2017/070719
§ 371 (c)(1),
(2) Date: Jul. 19, 2017

(87) PCT Pub. No.: WO2017/215259
PCT Pub. Date: Dec. 21, 2017

(65) Prior Publication Data
US 2018/0211087 A1    Jul. 26, 2018

(30) Foreign Application Priority Data

Jun. 15, 2016   (CN) .......................... 2016 1 0422613

(51) Int. Cl.
*G06K 9/00*   (2006.01)
*G02F 1/13*   (2006.01)
*G02F 1/1335*   (2006.01)

(52) U.S. Cl.
CPC .......... *G06K 9/0004* (2013.01); *G02F 1/132* (2013.01); *G02F 1/133555* (2013.01); *G06K 9/00* (2013.01)

(58) Field of Classification Search
CPC .... G06K 9/00; G06K 9/0004; G06K 9/00006; G06K 9/00013; G06K 9/00053; G02F 1/132; G02F 1/133555
See application file for complete search history.

(56) References Cited

U.S. PATENT DOCUMENTS

| 4,120,585 A | 10/1978 | De Palma |
| 6,310,683 B1 * | 10/2001 | Fujiwara .............. G06K 9/0004 250/556 |

(Continued)

FOREIGN PATENT DOCUMENTS

| CN | 1209612 A | 3/1999 |
| CN | 203838722 U | 9/2014 |

(Continued)

OTHER PUBLICATIONS

International Search Report and Written Opinion in PCT/CN2017/070719 dated Mar. 10, 2017.

*Primary Examiner* — Jia X Pan
(74) *Attorney, Agent, or Firm* — Womble Bond Dickinson (US) LLP

(57) ABSTRACT

The present disclosure provides a fingerprint recognition device, a manufacturing method thereof, and a liquid crystal display comprising a fingerprint recognition device. The fingerprint recognition device comprises: a recognition element; a light-reflecting element arranged above the recognition element; and a temperature-sensitive liquid crystal layer arranged between the recognition element and the light-reflecting element. The recognition element comprises (Continued)

a plurality of recognition units, each of which includes a light-emitting sub-unit and a photosensitive sub-unit.

20 Claims, 4 Drawing Sheets

(56) References Cited

U.S. PATENT DOCUMENTS

| | | | | |
|---|---|---|---|---|
| 2017/0249494 A1* | 8/2017 | Zhang | ................ | G06K 9/00013 |
| 2018/0060642 A1* | 3/2018 | Kim | ....................... | G02B 5/045 |
| 2018/0165496 A1* | 6/2018 | Cheng | ................... | G02F 1/1333 |

FOREIGN PATENT DOCUMENTS

| | | |
|---|---|---|
| CN | 204028936 U | 12/2014 |
| CN | 204463157 U | 7/2015 |
| CN | 105844270 A | 8/2016 |

* cited by examiner

FINGERPRINT RECOGNITION DEVICE, MANUFACTURING METHOD THEREOF, LIQUID CRYSTAL DISPLAY

RELATED APPLICATION

The present application is the U.S. national phase entry of PCT/CN2017/070719, with an international filing date of Jan. 10, 2017, which claims the benefit of Chinese Patent Application No. 201610422613.3, filed on Jun. 15, 2016, the entire disclosure of which is incorporated herein by reference.

FIELD

The present disclosure generally relates to the field of fingerprint recognition, and more particularly to a fingerprint recognition device, a manufacturing method thereof, and a liquid crystal display comprising a fingerprint recognition device.

BACKGROUND

With the progress in modern society, the importance of personal identity recognition and personal information security has gradually attracted people's attention. Due to uniqueness and invariability of the human fingerprint, the fingerprint recognition technology is characterized by good security, high reliability, and being simple and convenient to use, thus it is widely used in a variety of fields for protecting personal information security, including display field, especially the field of electronic devices having display function, such as a mobile phones, a notebook computer, a tablet computer, a digital camera, and so on. The fingerprint recognition function has become one of the essential functions of an existing electronic device, which is of great significance for enhancing the security of the electronic device, extending the application range thereof, etc.

The current fingerprint recognition technology mainly includes optical fingerprint recognition technology, capacitive fingerprint recognition technology, and so on. The optical fingerprint recognition technology scans a surface of finger skin by means of light, and compares the scanned picture with the prestored picture to realize fingerprint recognition. However, in this case, cleanliness of the finger surface has a direct impact on the recognition effect. If a lot of dust adheres to the user's finger, incorrect recognition would be likely to take place. Moreover, if someone makes a fingerprint mold according to the finger, the mold may also pass the recognition system. Therefore, the optical fingerprint recognition technology is not safe and stable enough.

The capacitive fingerprint recognition technology is currently the mainstream fingerprint recognition technology, which employs capacitor plates arranged alternately. When a finger touches the capacitor plates, valleys and ridges of the fingerprint act as dielectrics between the capacitor plates. By sensing the difference in the capacitance variation between the capacitors, a distribution of the valleys and the ridges of the fingerprint can be obtained.

However, when the above fingerprint recognition technology is applied to an electronic device, it is often incapable of integrating well with the electronic device. It is common to add a separate fingerprint recognition module to the electronic device, which increases the volume of the electronic device and is detrimental to the miniaturization of the electronic device, resulting in a reduction in the integration level of the electronic device. Moreover, the fingerprint recognition module as a separate module is susceptible to attacks and violent dismantling, which is disadvantageous to the protection of personal information.

Accordingly, there is a need in the art for providing an improved fingerprint recognition device.

SUMMARY

It is an objective of the present disclosure to provide a fingerprint recognition device, a manufacturing method thereof, and a liquid crystal display comprising a fingerprint recognition device, which are capable of at least partially alleviating or eliminating one or more of the above-mentioned problems in the prior art.

According to a first aspect of the present disclosure, there is provided a fingerprint recognition device comprising: a recognition element; a light-reflecting element arranged above the recognition element; and a temperature-sensitive liquid crystal layer arranged between the recognition element and the light-reflecting element, wherein the recognition element comprises a plurality of recognition units, each recognition unit comprising a light-emitting sub-unit and a photosensitive sub-unit.

In the fingerprint recognition device described above, the temperature-sensitive liquid crystal layer acts as a functional layer. When a finger touches the fingerprint recognition device, since the ridges and the valleys of the fingerprint contact the fingerprint recognition device (specifically, the liquid crystal layer) at different degrees, heat amounts received by the liquid crystal layer at the positions corresponding to the ridges and the valleys are different. This difference in heat amounts results in different degrees of variation in the liquid crystal morphology of the liquid crystal layer at the positions corresponding to the ridges and the valleys, which is macroscopically represented by the difference in the refractive indexes of the liquid crystals at the positions corresponding to the ridges and the valleys. In this case, when light emitted by the light-emitting sub-unit is incident on the light-reflecting element through the liquid crystal layer and is reflected back by the light-reflecting element through the liquid crystal layer to the photosensitive sub-unit, since the light is refracted at the liquid crystal layer/recognition element interface, and the refraction angle is related to the refractive index of the liquid crystal layer, incident angles of the light incident on the recognition element are different, such that the illumination intensities sensed by the photosensitive sub-units at the positions corresponding to the ridges and the valleys are different. Consequently, the ridges and the valleys of the fingerprint can be distinguished based on the illumination intensities sensed by the photosensitive sub-units, thereby realizing the fingerprint recognition function.

Unlike the existing optical fingerprint recognition technology and capacitive fingerprint recognition technology, the fingerprint recognition device in embodiments of the present disclosure utilizes the temperature-sensitive characteristic of the liquid crystal layer to recognize the ridges and the valleys of the fingerprint. Since the ridges and the valleys of the finger apply different heat amounts on the liquid crystal layer, even if the user's finger surface has low cleanliness, the impact on the recognition effect is not significant. In addition, since the fingerprint is recognized using the heat amount generated upon contact of the user's finger with the fingerprint recognition device, the fingerprint mold made according to the finger cannot pass the recognition system. Therefore, the fingerprint recognition device in embodiments of the present disclosure is more secure and stable.

In some embodiments, a temperature sensitivity of the temperature-sensitive liquid crystal layer is at least 0.1° C. Experiments indicate that such temperature sensitivity can effectively ensure that the fingerprint recognition device distinguishes the ridges and the valleys of the finger.

In some embodiments, the temperature-sensitive liquid crystal layer includes 4-methoxybenzylidene-4'-butylaniline.

In some embodiments, the fingerprint recognition device further comprises a thermally conductive element arranged above the light-reflecting element. The presence of the thermally conductive element enables heat on the finger to be sufficiently conducted to the liquid crystal layer, thereby improving the sensitivity and accuracy of fingerprint recognition.

In some embodiments, the thermally conductive element is a longitudinal thermally conductive layer, which is capable of conducting heat on the finger longitudinally to the liquid crystal layer and almost conducts no heat transversely, thereby reducing loss of heat and improving the sensitivity and accuracy of fingerprint recognition.

In some embodiments, the thermally conductive element is made of a carbon nanotube composite material. Carbon nanotube, as a one-dimensional nano-material, has light weight and perfectly connected hexagonal structures, and has many unusual mechanical, electrical and chemical properties, among which the most eye-catching thermal property is thermal conductivity coefficient. It is theoretically predicted that the carbon nanotube becomes a material having the highest thermal conductivity coefficient in the world for the thermal conductivity coefficient thereof is likely to be greater than that of diamond. Therefore, it is desirable to use a carbon nanotube composite material to make the thermally conductive element.

In some embodiments, the thermally conductive element has a plurality of parallel strip-shaped units, each of which extends in a longitudinal direction of the liquid crystal layer. The strip-shaped units of the thermally conductive element may be formed by laser cutting or chemical etching. The plurality of parallel and longitudinally extending strip-shaped units are capable of efficiently conducting heat on the finger to the liquid crystal layer while not conducting heat transversely, thereby minimizing loss of heat.

In some embodiments, the fingerprint recognition device further comprises a protection element arranged above the thermally conductive element. The protection element is configured to protect the underlying thermally conductive element and should have good conductivity for heat. For example, the protection element may be made of tempered glass or plexiglass.

In some embodiments, the photosensitive sub-unit is made of a semiconductor material having photosensitivity, for example, a silver salt photosensitive material, a non-silver salt photosensitive material, etc.

In some embodiments, the light-emitting sub-unit comprises a laser. The laser light emitted by the laser has advantages including good directionality, high luminance, pure color, high energy, and so on, and the illumination angle thereof is easy to control. When a laser is used as the light-emitting sub-unit, most of the laser light emitted by the laser can be reflected back to the recognition element by the light-reflecting element and sensed by the photosensitive sub-unit in the recognition element. Therefore, the accuracy of the fingerprint recognition device can be improved.

According to a second aspect of the present disclosure, there is provided a liquid crystal display, in which the fingerprint recognition device according to the first aspect of the present disclosure is integrated, and the light-reflecting element of the fingerprint recognition device is a transflective element.

In the above liquid crystal display, the light-emitting sub-unit of the fingerprint recognition device acts, on one hand, as a light source in the fingerprint recognition device, and on the other hand, as a backlight of the liquid crystal display. When light emitted by the light-emitting sub-unit is incident on the light-reflecting element, a part is reflected, thereby realizing the fingerprint recognition function, and another part is transmitted, thereby realizing the display function of the liquid crystal display.

In some embodiments, the temperature-sensitive liquid crystal layer of the fingerprint recognition device and a liquid crystal layer of the liquid crystal display are formed of the same material in the same layer. In such a liquid crystal display, the fingerprint recognition device can be formed integrally with the liquid crystal display, and the liquid crystal display is not added with a separate fingerprint recognition module, without increasing the volume of the liquid crystal display and facilitates improvement of the miniaturization and integration level of the liquid crystal display. Moreover, the fingerprint recognition module integrated in the liquid crystal display is not susceptible to attacks and violent dismantling, which is advantageous to the protection of personal information.

According to a third aspect of the present disclosure, there is provided a method of manufacturing a fingerprint recognition device, comprising: providing a recognition element comprising a plurality of recognition units, each recognition unit comprising a light-emitting sub-unit and a photosensitive sub-unit; forming, above the recognition element, a temperature-sensitive liquid crystal layer and a light-reflecting element successively.

In some embodiments, the light-reflecting element is formed by making a light-reflecting material layer on a base substrate by vapor deposition or plating process. For example, the light-reflecting material layer may be silver. The light-reflecting element made by such a method has simple manufacturing process and excellent light-reflecting performance.

In some embodiments, the above manufacturing method further comprises forming a thermally conductive element above the light-reflecting element. The thermally conductive element has a plurality of parallel strip-shaped units by means of laser cutting or chemical etching, each strip-shaped unit extending in the longitudinal direction of the liquid crystal layer.

It is to be noted that the second and third aspects of the present disclosure have similar or the same example implementations and benefits as the first aspect of the present disclosure, which will not be described here for simplicity.

These and other aspects of the present disclosure will be apparent from and elucidated with reference to the embodiments described hereinafter.

DETAILED DESCRIPTION

Figure 1:
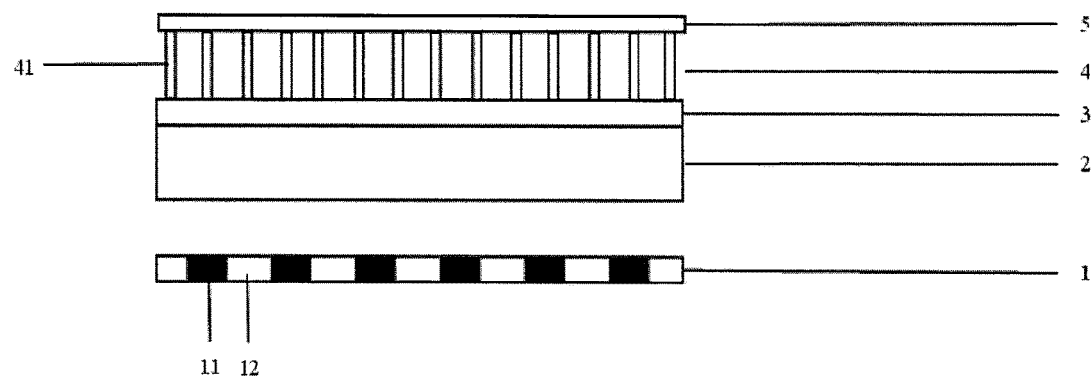
FIG. 1 illustrates a structural schematic view of a fingerprint recognition device according to embodiments of the present disclosure.

Exemplary embodiments of the present disclosure will be described in detail below with reference to the accompanying drawings. The drawings are schematic and are not necessarily drawn to scale, which are merely illustrative of the embodiments of the present disclosure and are not intended to limit the scope of the present disclosure. In the drawings, the same reference numerals denote the same or similar parts. In order to make the technical solutions of the present disclosure clearer, process steps and device structures well known in the art are omitted here.

FIG. 1 illustrates a schematic structural view of a fingerprint recognition device according to embodiments of the present disclosure. As shown in FIG. 1, the fingerprint recognition device comprises a recognition element 1, a light-reflecting element 3 arranged above the recognition element 1, and a temperature-sensitive liquid crystal layer 2 arranged between the recognition element 1 and the light-reflecting element 3. The temperature sensitivity of the temperature-sensitive liquid crystal layer 2 is at least 0.1° C.

The recognition element 1 comprises a plurality of recognition units, each of which comprises a light-emitting sub-unit 11 and a photosensitive sub-unit 12. As shown in FIG. 1, the light-emitting sub-unit 11 and the photosensitive sub-unit 12 are arranged alternately and have a rectangular shape. However, as will be appreciated by those skilled in the art, the light-emitting sub-unit 11 and the photosensitive sub-unit 12 may be arranged in other ways and may have other shapes, such as a circle, a square, etc., as long as, in specific cases (e.g. when a finger does not touch the fingerprint recognition device), light emitted by the light-emitting sub-unit 11 can be incident on the photosensitive sub-unit 12 after being reflected by the light-reflecting element 3. As shown in FIG. 1, there is a gap between the recognition element 1 and the liquid crystal layer 2, which may be filled with a certain material (e.g. air), or may be vacuum, as long as it is ensured that the refractive index of the gap is different from that of the liquid crystal layer 2 and light is refracted at the liquid crystal layer/gap interface. Alternatively, in other embodiments, there may be no gap between the recognition element and the liquid crystal layer.

As shown in FIG. 1, the fingerprint recognition device further comprises a thermally conductive element 4 arranged above the light-reflecting element 3. The presence of the thermally conductive element 4 enables heat on the finger to be sufficiently conducted to the liquid crystal layer, thereby improving the sensitivity and accuracy of fingerprint recognition. In particular, the thermally conductive element 4 is a longitudinally conductive layer, which is capable of conducting heat on the finger longitudinally to the liquid crystal layer and almost conducts no heat transversely, thereby reducing loss of heat and improving the sensitivity and accuracy of fingerprint recognition. Optionally, the thermally conductive element 4 is made of a carbon nanotube composite material and has a plurality of parallel strip-shaped units 41, each of which extends in the longitudinal direction of the liquid crystal layer 2. The plurality of parallel and longitudinally extending strip-shaped units 41 are capable of efficiently conducting heat on the finger to the liquid crystal layer while not conducting heat transversely, thereby minimizing loss of heat.

Further, the fingerprint recognition device further comprises a protection element 5 arranged above the thermally conductive element 4. The protection element 5 is configured to protect the underlying thermally conductive element 4 and should have good conductivity for heat. For example, the protection element may be made of tempered glass or plexiglass.

The photosensitive sub-unit 12 is made of a semiconductor material having photosensitivity, such as a silver salt photosensitive material, a non-silver salt photosensitive material, and the like.

The light-emitting sub-unit 11 includes a laser. When a laser is used as the light-emitting sub-unit 11, most of the laser light emitted by the laser can be reflected back to the recognition element 1 by the light-reflecting element 3 and sensed by the photosensitive sub-unit 12 in the recognition element 1. Therefore, the accuracy of the fingerprint recognition device can be improved.

Figure 5:
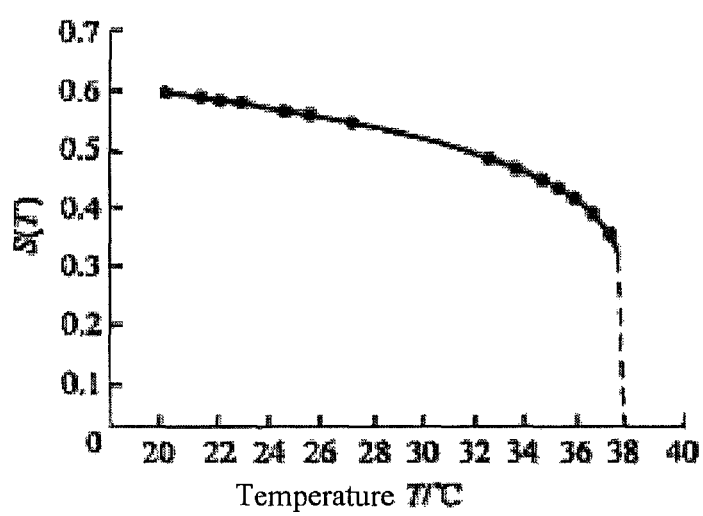
FIG. 5 illustrates a graph showing a variation of the liquid crystal order parameter of typical liquid crystal 4-methoxybenzylidene-4'-butylaniline (MBBA) with temperature.

The ordering degree of arrangement of liquid crystal molecules directly affects the anisotropy of their physical properties such as refractive index, dielectric constant, magnetic susceptibility, and so on. The metric of the ordering degree of arrangement of liquid crystal molecules is given by an order parameter S. FIG. 5 illustrates a graph showing a variation of the value of the liquid crystal order parameter S of typical liquid crystal 4-methoxybenzylidene-4'-butylaniline (MBBA) with temperature. As can be seen from FIG. 5, the order parameter varies monotonously and continuously with temperature. Therefore, in the fingerprint recognition device described above, the temperature-sensitive liquid crystal layer acts as a functional layer. When a finger touches the fingerprint recognition device, since the ridges and the valleys of the fingerprint contact the fingerprint recognition device (specifically, the liquid crystal layer) at different degrees, heat amounts received by the liquid crystal layer at the positions corresponding to the ridges and the valleys are different. This difference in heat amounts results in different degrees of variation in the liquid crystal morphology of the liquid crystal layer at the positions corresponding to the ridges and the valleys, which is macroscopically represented by the difference in the refractive indexes of the liquid crystals at the positions corresponding to the ridges and the valleys. In this case, when light emitted by the light-emitting sub-unit is incident on the light-reflecting element through the liquid crystal layer and is reflected back by the light-reflecting element through the liquid crystal layer to the photosensitive sub-unit, since the light is refracted at the liquid crystal layer/recognition element (in FIG. 1, specifically, the gap between the liquid crystal layer and the recognition element) interface, and the refraction angle is related to the refractive index of the liquid crystal layer, incident angles of the light incident on the recognition element are different, such that the illumination intensities sensed by the photosensitive sub-units at the positions corresponding to the ridges and the valleys are different. Consequently, the ridges and the valleys of the fingerprint can be distinguished based on the illumination intensities sensed by the photosensitive sub-units, thereby realizing the fingerprint recognition function.

Unlike the existing optical fingerprint recognition technology and capacitive fingerprint recognition technology, the fingerprint recognition device in embodiments of the present disclosure utilizes the temperature-sensitive characteristic of the liquid crystal layer to recognize the ridges and the valleys of the fingerprint. Since the ridges and the valleys of the finger apply different heat amounts on the liquid crystal layer, even if the user's finger surface has low cleanliness, the impact on the recognition effect is not significant. In addition, since the fingerprint is recognized using the heat amount generated upon contact of the user's finger with the fingerprint recognition device, the fingerprint mold made according to the finger cannot pass the recognition system. Therefore, the fingerprint recognition device in embodiments of the present disclosure is more secure and stable.

Figure 2:
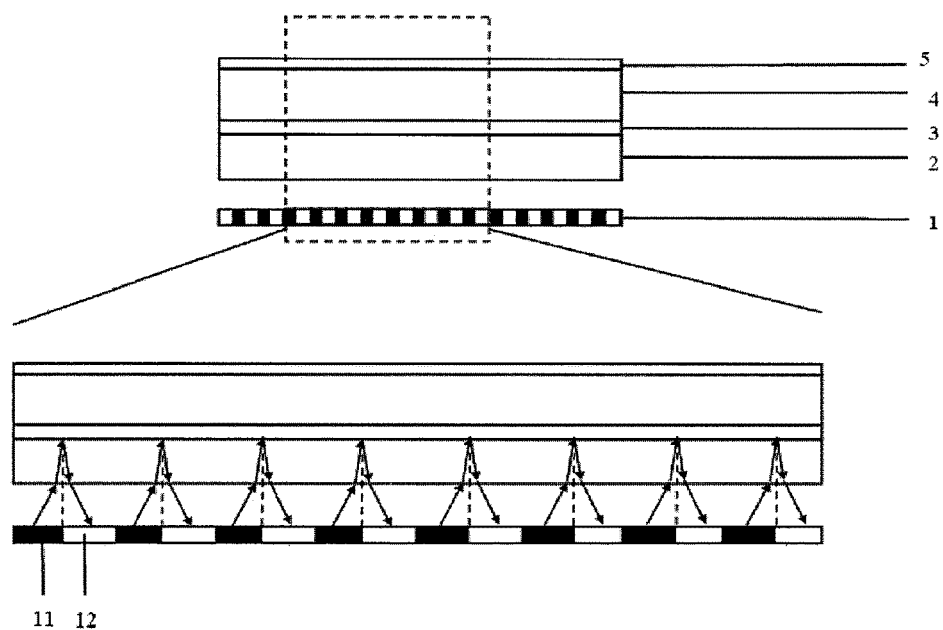
FIG. 2 illustrates an optical path diagram when a finger does not touch the fingerprint recognition device according to embodiments of the present disclosure.

FIG. 2 illustrates an optical path diagram when a finger does not touch the fingerprint recognition device according to embodiments of the present disclosure. As shown in FIG. 2, when a finger does not touch the fingerprint recognition device, light emitted by each of the light-emitting sub-units 11 is reflected by the light-reflecting element 3 after passing through the liquid crystal layer 2, and is incident on a corresponding photosensitive sub-unit 12 after passing through the liquid crystal layer 2 again, wherein it is refracted at the liquid crystal layer/gap interface. However, as will be appreciated by those skilled in the art, when the finger does not touch the fingerprint recognition device, the fingerprint recognition device may also be configured such that light emitted by each of the light-emitting sub-units is reflected by the light-reflecting element after passing through the liquid crystal layer, while is not incident on a corresponding photosensitive sub-unit after passing through the liquid crystal layer again, but is incident, for example, on an adjacent light-emitting sub-unit.

Figure 3:
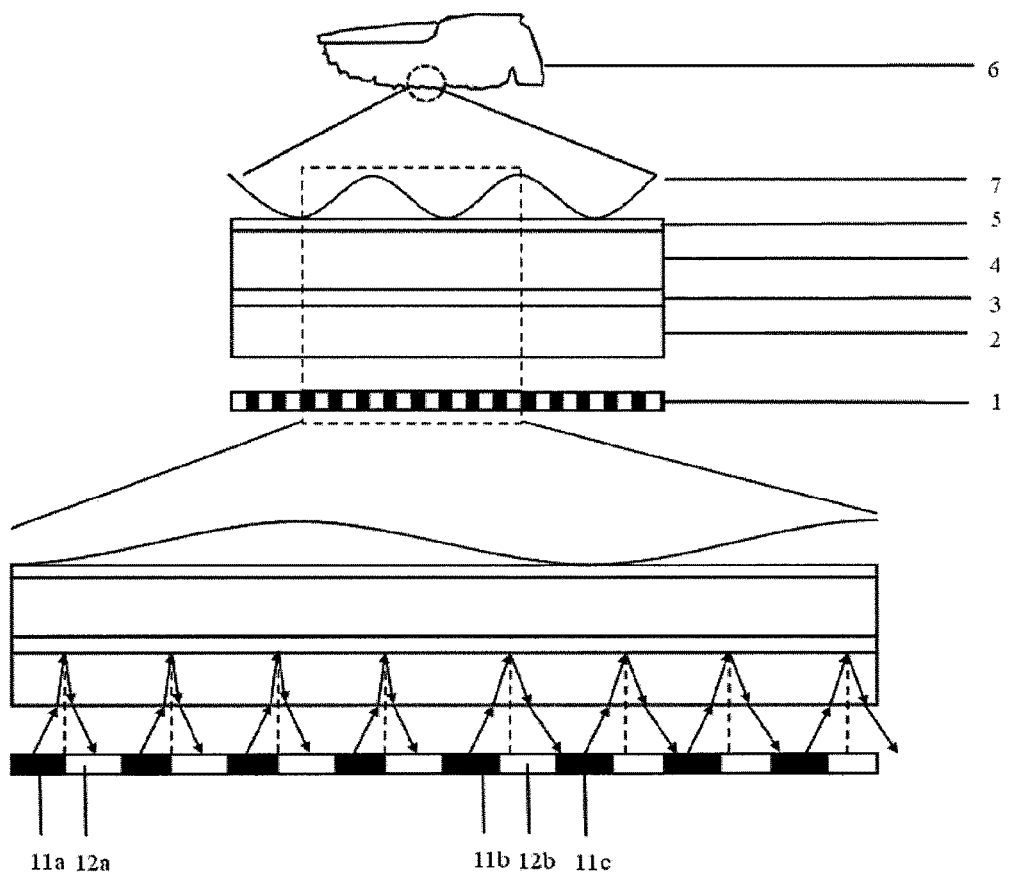
FIG. 3 illustrates an optical path diagram when a finger touches the fingerprint recognition device according to embodiments of the present disclosure.

FIG. 3 illustrates an optical path diagram when a finger touches the fingerprint recognition device according to embodiments of the present disclosure. As shown in FIG. 3, when a finger 6 touches the fingerprint recognition device, the ridges of a fingerprint 7 are in contact with the fingerprint recognition device, while the valleys of the fingerprint 7 are not in contact with the fingerprint recognition device. The liquid crystal layer at the positions in contact with the ridges of the fingerprint 7 receives heat of the finger, so the refractive index is changed. The liquid crystal layer at the positions corresponding to the valleys of the fingerprint 7 does not receive heat of the finger, so the refractive index is not changed. Compared to the situation shown in FIG. 2, light emitted by each of the light-emitting sub-units 11a at the positions corresponding to the valleys of the fingerprint 7 is reflected by the light-reflecting element 3 after passing through the liquid crystal layer 2, and is incident on a corresponding photosensitive sub-unit 12a after passing through the liquid crystal layer 2 again. However, light emitted by each of the light-emitting sub-units 11b at the positions corresponding to the ridges of the fingerprint 7 is reflected by the light-reflecting element 3 after passing through the liquid crystal layer 2, and is not incident on a corresponding photosensitive sub-unit 12b after passing through the liquid crystal layer 2 again, since the refractive index of the liquid crystal layer 2 is changed, but is incident on an adjacent light-emitting sub-unit 11c. Therefore, the illumination intensities sensed by the photosensitive sub-units 12a and 12b are different, whereby the recognition element is able to recognize the ridges and the valleys of the fingerprint.

As will be appreciated by those skilled in the art, the fingerprint recognition device may also be configured such that light emitted by each of the light-emitting sub-units at the positions corresponding to the valleys of the fingerprint is not incident on a corresponding photosensitive sub-unit, but is incident, for example, on an adjacent light-emitting sub-unit, and light emitted by each of the light-emitting sub-units at the positions corresponding to the ridges of the fingerprint is incident on a corresponding photosensitive sub-unit, as long as the illumination intensities sensed by the photosensitive sub-units at the positions corresponding to the ridges and the valleys of the fingerprint are different.

Embodiments of the present disclosure further provide a liquid crystal display in which the fingerprint recognition device shown in FIG. 1 is integrated and the light-reflecting element 3 (FIG. 1) of the fingerprint recognition device is a transflective element. The temperature-sensitive liquid crystal layer 2 of the fingerprint recognition device and a liquid crystal layer of the liquid crystal display are formed of the same material in the same layer.

In the above liquid crystal display, the light-emitting sub-unit in the fingerprint recognition device acts, on one hand, as a light source in the fingerprint recognition device, and on the other hand, as a backlight of the liquid crystal display. When light emitted by the light-emitting sub-unit is incident on the light-reflecting element, a part is reflected, thereby realizing the fingerprint recognition function, and another part is transmitted, thereby realizing the display function of the liquid crystal display.

Figure 4:
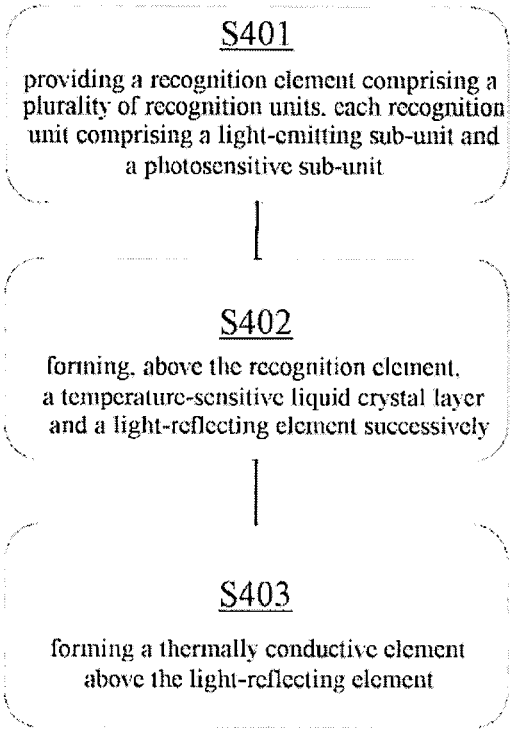
FIG. 4 illustrates a flow chart of a method of manufacturing a fingerprint recognition device according to embodiments of the present disclosure.

FIG. 4 illustrates a flow chart of a method of manufacturing a fingerprint recognition device according to embodiments of the present disclosure. As shown in FIG. 4, at step S401, a recognition element is provided. The recognition element comprises a plurality of recognition units, each of which comprises a light-emitting sub-unit and a photosensitive sub-unit. At step S402, a temperature-sensitive liquid crystal layer and a light-reflecting element are formed above the recognition element successively. Optionally, at step S403, a thermally conductive element is formed above the light-reflecting element. The thermally conductive element has a plurality of parallel strip-shaped units by means of laser cutting or chemical etching, each of which extends in the longitudinal direction of the liquid crystal layer.

In the above method, the light-reflecting element is formed by making a light-reflecting material layer on a base substrate by vapor deposition or plating process. For example, the light-reflecting material layer may be silver. The light-reflecting element made by such a method has simple manufacturing process and excellent light-reflecting performance.

The concept of the present disclosure can be widely applied to any system having liquid crystal display function, including a desktop computer, a laptop computer, a mobile phone, a tablet computer, and the like. In addition, although several embodiments have been described in detail above, other modifications are possible. For example, the flow chart described above does not require the particular order or sequence as described to achieve the desired results. Other steps may be provided, or steps may be removed from the described flow, and other components may be added to the described system or removed from the described system. Other embodiments may be within the scope of the present disclosure. Numerous variations and modifications may be made by those skilled in the art in view of the teachings of the present disclosure without departing from the spirit and scope of the present disclosure.

The invention claimed is:

1. A fingerprint recognition device comprising:
  a recognition element;
  a light-reflecting element arranged above the recognition element; and a temperature-sensitive liquid crystal layer arranged between the recognition element and the light-reflecting element, wherein the recognition element comprises a plurality of recognition units, each recognition unit comprising a light-emitting sub-unit and a photosensitive sub-unit.

2. The fingerprint recognition device according to claim 1, wherein a temperature sensitivity of the temperature-sensitive liquid crystal layer is at least 0.1° C.

3. The fingerprint recognition device according to claim 2, wherein the temperature-sensitive liquid crystal layer includes 4-methoxybenzylidene-4'-butylaniline.

4. The fingerprint recognition device according to claim 1, further comprising a thermally conductive element arranged above the light-reflecting element.

5. The fingerprint recognition device according to claim 4, wherein the thermally conductive element is a longitudinal thermally conductive layer.

6. The fingerprint recognition device according to claim 5, wherein the thermally conductive element has a plurality of parallel strip-shaped units, each of which extends in a longitudinal direction of the liquid crystal layer.

7. The fingerprint recognition device according to claim 4, further comprising a protection element arranged above the thermally conductive element.

8. The fingerprint recognition device according to claim 1, wherein the photosensitive sub-unit is made of a semiconductor material having photosensitivity.

9. The fingerprint recognition device according to claim 8, wherein the semiconductor material is selected from a group comprising a silver salt photosensitive material and a non-silver salt photosensitive material.

10. The fingerprint recognition device according to claim 1, wherein the light-emitting sub-unit comprises a laser.

11. The fingerprint recognition device according to claim 4, wherein the thermally conductive element is made of a carbon nanotube composite material.

12. The fingerprint recognition device according to claim 5, wherein the thermally conductive element is made of a carbon nanotube composite material.

13. The fingerprint recognition device according to claim 7, wherein the protection element is made of tempered glass.

14. The fingerprint recognition device according to claim 7, wherein the protection element is made of plexiglass.

15. A method of manufacturing a fingerprint recognition device, comprising:

providing a recognition element comprising a plurality of recognition units, each recognition unit comprising a light-emitting sub-unit and a photosensitive sub-unit;

forming, above the recognition element, a temperature-sensitive liquid crystal layer and a light-reflecting element successively.

16. The method according to claim 15, wherein the light-reflecting element is formed by making a light-reflecting material layer on a base substrate by vapor deposition or plating process.

17. The method according to claim 16, wherein the light-reflecting material layer is silver.

18. The method according to claim 16, further comprising forming a thermally conductive element above the light-reflecting element, the thermally conductive element having a plurality of parallel strip-shaped units by means of laser cutting or chemical etching, wherein each strip-shaped unit extends in a longitudinal direction of the liquid crystal layer.

19. A liquid crystal display, comprising a fingerprint recognition device which is integrated in the liquid crystal display, wherein the fingerprint recognition device comprises:

a recognition element;

a light-reflecting element arranged above the recognition element; and a temperature-sensitive liquid crystal layer arranged between the recognition element and the light-reflecting element, the recognition element comprises a plurality of recognition units, each recognition unit comprising a light-emitting sub-unit and a photosensitive sub-unit, and the light-reflecting element is a transflective element.

20. The liquid crystal display according to claim 19, wherein the temperature-sensitive liquid crystal layer and a liquid crystal layer of the liquid crystal display are formed of a same material in a same layer.

* * * * *